United States Patent [19]

Wyness et al.

[11] Patent Number: 5,124,301
[45] Date of Patent: Jun. 23, 1992

[54] HIGHLY ALKALINE TRANSESTERIFICATION CATALYST, E.G., ALKALI METAL ALKOXIDE, PROTECTED BY FATTY ACID ESTERS

[75] Inventors: Glen R. Wyness, Cincinnati; John K. Howie, Oregonia, both of Ohio

[73] Assignee: The Procter & Gamble Company, Cincinnati, Ohio

[21] Appl. No.: 577,412

[22] Filed: Sep. 4, 1990

[51] Int. Cl.$^5$ .................... B01J 31/12; B01J 31/02
[52] U.S. Cl. .................... 502/171; 502/150; 502/173
[58] Field of Search .................... 502/150, 171, 173

[56] References Cited

U.S. PATENT DOCUMENTS

| | | | |
|---|---|---|---|
| 2,609,346 | 9/1952 | Faulkner | 502/173 |
| 3,600,186 | 8/1971 | Mattson et al. | 99/1 |
| 3,856,703 | 12/1974 | Muller et al. | 502/173 X |
| 3,963,699 | 6/1976 | Rizzi et al. | 260/234 R |
| 4,169,101 | 9/1979 | Ucciani et al. | 502/173 X |
| 4,517,360 | 5/1985 | Volpenhein | 536/119 |
| 4,518,772 | 5/1985 | Volpenhein | 536/119 |

FOREIGN PATENT DOCUMENTS

| | | | |
|---|---|---|---|
| 1584584 | 11/1969 | France | 502/173 |
| 51-14486 | 5/1986 | Japan. | |
| 684477 | 7/1968 | South Africa. | |

*Primary Examiner*—Patrick P. Garvin
*Attorney, Agent, or Firm*—Eric W. Guttag; Robert B. Aylor; Richard C. Witte

[57] ABSTRACT

Highly alkaline transesterification catalysts like alkali metal alkoxides, which are not stable in the atmosphere, are stabilized by surrounding them with fatty acid esters of volatile alcohols. These fatty acid esters of volatile alcohols are preferably solid and/or, preferably, are the same as one of the reactants in the transesterification reaction that is being catalyzed.

14 Claims, No Drawings

HIGHLY ALKALINE TRANSESTERIFICATION CATALYST, E.G., ALKALI METAL ALKOXIDE, PROTECTED BY FATTY ACID ESTERS

TECHNICAL FIELD

This invention relates to improved catalysts for use, e.g., in the synthesis of higher polyol fatty acid polyesters, especially sucrose polyesters, via transesterification.

BACKGROUND OF THE INVENTION

Transesterification reactions for preparing polyol fatty acid polyesters have been described in U.S. Pat. No. 3,963,699, Rizzi et al., issued Jun. 15, 1976; U.S. Pat. No. 4,517,360, Volpenhein, issued May 14, 1985; and U.S. Pat. No. 4,518,772, Volpenhein, issued May 21, 1985; all of said patents being incorporated herein by reference.

In order to have highly reactive alkaline catalysts such as alkali metal alkoxides readily available for use in commercial processes, it is necessary to stabilize the catalyst.

SUMMARY OF THE INVENTION

The present invention relates to stable, highly alkaline, transesterification catalyst compositions, suitable for use in transesterification processes for synthesizing higher polyol fatty acid polyesters from polyol and fatty acid ester, which comprise normally unstable, highly alkaline, transesterification catalysts surrounded by, e.g., encapsulated or suspended in, fatty acid ester, preferably, in said fatty acid ester reactant, more preferably ester of fatty acid containing from about 12 to about 22, preferably from about 16 to about 22, more preferably from about 16 to about 18 carbon atoms. The alcohol portion of said fatty acid ester reactant is derived from volatile alcohol, preferably an alkyl alcohol containing from about 1 to about 4, preferably from about 1 to about 2, more preferably one, carbon atoms, or other volatile alcohol such as 2-methoxy ethanol or benzyl alcohol.

DETAILED DESCRIPTION OF THE INVENTION

The invention relates to unstable, highly alkaline, highly reactive, transesterification catalysts, especially alkali metal alkoxides and more especially sodium or potassium methoxide, ethoxide, or t-butoxide. More preferably, the catalyst is sodium or potassium methoxide, encapsulated or suspended in $C_{12-22}$ fatty acid ester of volatile alcohol, preferably short chain alkyl ($C_{1-4}$) alcohols, and especially those esters that are reactants in the reaction being catalyzed. Solid esters are desirable. The short chain alcohol preferably corresponds to any alkoxide catalyst that is being encapsulated. The fatty acid preferably has from about 16 to about 22 carbon atoms as set forth hereinbefore and exemplified hereinafter. The catalyst is any catalyst that is unstable in storage so as to require protection. Encapsulated, or suspended (protected), catalyst is desirable for use in commercial processes to minimize loss of activity. This simplifies the accurate measurement of catalyst for use in the transesterification reaction. The protected catalyst can also be handled more safely.

Typically, the protected catalyst will comprise from about 1% to about 60%, preferably from about 5% to about 40%, more preferably from about 10% to about 20%, of catalyst and the remainder is, preferably, essentially said fatty acid ester, preferably reactant ester, described in detail hereinafter.

The Fatty Acid Esters

As used herein, the term "fatty acid ester" is intended to include the $C_1$-$C_4$ (preferably methyl), 2-methoxy ethyl and/or benzyl esters of fatty acids containing at least about twelve carbon atoms, and mixtures of such esters with esters of other acids. Suitable reactant esters can be prepared by the reaction of diazoalkanes and fatty acids, or derived by alcoholysis from the fatty acids naturally occurring in fats and oils. Suitable fatty acid esters can be derived from either synthetic or natural, saturated or unsaturated, fatty acids and include positional and geometrical isomers. Suitable preferred saturated fatty acids include, for example, caprylic, capric, lauric, myristic, palmitic, stearic, behenic, isomyristic, isomargaric, myristic, caprylic, and anteisoarachadic. Suitable preferred unsaturated fatty acids include, for example, myristoleic, palmitoleic, ricinoleic, linoleic, oleic, elaidic, linolenic, eleasteric, arachidic, arachidonic, erucic, and erythrogenic acids. Mixtures of fatty acids derived from soybean oil, palm oil, safflower oil, rapeseed oil, canola oil, cottonseed oil, and corn oil are especially preferred for use herein. For example, rapeseed provides a good source for $C_{22}$ fatty acid. $C_{16}$-$C_{18}$ fatty acid can be provided by tallow, soybean oil, or cottonseed oil. Shorter chain fatty acids can be provided by coconut, palm kernel, or babassu oils. Corn oil, lard, olive oil, palm oil, peanut oil, safflower seed oil, sesame seed oil, and sunflower seed oil, are examples of other natural oils which can serve as the source of the fatty acid component. Methyl esters are the preferred fatty acid esters for use herein, since their use in transesterification processes to produce polyol fatty acid esters tends to result in unusually high yields.

It is preferred that these fatty acid esters be highly purified to remove color/odor materials, oxidation products, and their precursors. Such materials include those that have a color, odor or taste that is objectionable, or which develop an objectionable color, odor, or taste upon heat treatment and/or oxidation. In addition, highly polar materials which coat the catalyst surface should be removed. The free fatty acid level should be less than about 0.1%, preferably less than about 0.05%, by weight (typically measured as oleic acid) of the esters. Preferably, the carbonyl value, other than the carboxy carbonyls, should be less than 200 ppm, preferably less than 100 ppm, more preferably less than about 50 ppm. The percent transmittance at 375 nm with a heptane standard should be greater than zero, preferably greater than 60, most preferably greater than 80. For typical ester sources without added colored materials, these values define operable reactants. I.e., the carbonyl content is generally indicative of the total level of polar materials present. The low level of color/odor materials and/or oxidation products can be achieved by a combination of the process improvements set forth in U.S. Pat. No. 4,931.552, M. S. Gibson, L. N. Hawkins, M. M. Peffly, C. J. Kenneally, and P. J. Corrigan, issued Jun. 5, 1990, entitled "Production of Polyol Esters Having Reduced Color Content," said patent being incorporated herein by reference. In addition to having a low level of color/odor/oxidation materials and/or products, the fatty acid esters should have the lowest level of moisture possible, since any water present will react with the catalyst.

The Polyol

As used herein, the term "polyol" is intended to include any aliphatic or aromatic compound containing at least three free hydroxyl groups. In practicing the processes in which the catalysts disclosed herein are used, the selection of a suitable polyol is simply a matter of choice. For example, suitable polyols can be selected from the polyols disclosed in the Rizzi et al. and Volpenhein patents incorporated hereinbefore by reference.

Particularly preferred classes of materials suitable for use herein include the monosaccharides, the disaccharides and sugar alcohols. Preferred carbohydrates and sugar alcohols include xylitol, sorbitol and sucrose. The most preferred is sucrose.

The Catalyst

The highly alkaline catalysts which are encapsulated and that are generally suitable for use herein are those selected from the group consisting of alkali metals, such as sodium, lithium and potassium: alloys of two or more alkali metals, such as sodium-lithium and sodium-potassium alloys; alkali metal hydrides, such as sodium, lithium and potassium hydride; and the preferred alkali metal alkoxides, especially those containing from about one to about four carbon atoms such as potassium t-butoxide and sodium methoxide.

Other basic catalysts that can be used in transesterification reactions without encapsulation include potassium carbonate, sodium carbonate, barium carbonate, or mixtures of these compounds. These less reactive catalysts can increase yields of light colored higher polyol polyesters when used to initiate such reactions. Potassium carbonate is the most preferred of these less basic catalysts for use herein. These less reactive catalysts can optionally be used in the first stage(s) of the reaction, with the more highly alkaline catalyst being added in the second, or later, stage(s). In preferred reactions, the more highly alkaline catalyst is used in all stages. The use of these catalysts is further disclosed and claimed in U.S. Pat. No. 4,517,360, Volpenhein, issued May 14, 1985, entitled "Synthesis of Higher Polyol Fatty Acid Polyesters using Carbonate Catalysts," incorporated herein by reference.

The more reactive catalysts such as potassium or sodium methoxide should be protected, as set forth hereinbefore, until their addition into a reaction mixture. Preferably more reactive catalysts should be either suspended in, or more preferably, encapsulated by fatty acid ester, preferably fatty acid ester reactant.

Typical Reactions

In general, an initial heterogeneous reaction mixture comprises from about 10% to about 30%, preferably from about 14% to about 18%, by weight of polyol; from about 60% to about 0.5%, preferably from about 70% to about 80%, by weight of the fatty acid esters; from about 5% to about 20%, preferably from about 2% to about 10%, by weight of the emulsifier, e.g., alkali metal fatty acid soap; and from about 0.01% to about 1%, preferably from about 0.05% to about 0.1%, by weight of basic catalyst component. It is usually preferred to effect the reaction in at least two steps. Preferably, in the later step, or steps, additional fatty acid esters and the more reactive catalyst of this invention are added.

Reaction mixtures are typically heated to a temperature within the range from about 115° C. to about 150° C., preferably from about 130° C. to about 140° C., under a pressure of from about 0.1 mm to about 760 mm Hg, and preferably from about 0.3 mm to about 10 mm Hg.

All percentages, parts and ratios herein are by weight unless otherwise specified.

EXAMPLE

Encapsulated Potassium Methylate {Methoxide}

The reaction uses a 100 ml glass reactor fitted with a mechanical stirrer and a nitrogen inlet. About 20.0 grams of melted hardstock soybean methyl ester (I.V. ≦2.0) are added to the flask and heated to about 93° C. under nitrogen. About 5.0 grams of potassium methylate are then added and the mixture is heated at about 93° C. with vigorous agitation for 1 hour still under nitrogen. At this time the molten mixture is exposed to the atmosphere and is poured into a shallow pan and allowed to cool to room temperature. The encapsulated methylate is broken into chunks and ground in a blender. A sample is analyzed by titration with acid using an autotitrator. It is found to be about 13.7% potassium methylate and 27.4% potassium soap by weight, with the remainder being the soybean methyl ester.

Sucrose Polyester Preparation Using Encapsulated Potassium Methylate

The reaction uses a 1-liter glass reactor fitted with a thermometer, heating mantle, mechanical agitator, McLeod gauge, condenser, and temperature regulating device. Vacuum is drawn on the reactor with a mechanical vacuum pump.

To perform the first stage of the reaction, about 146 grams of partially hardened soybean methyl esters (0.5 mole) are added to the reactor along with about 25 grams of potassium stearate soap (0.08 mole), and about 1.4 grams of potassium carbonate catalyst (0.01 mole). To this mixture is added about 34.2 grams of crystalline sucrose (0.01 mole) with an average particle size of about 500 microns. This mixture is reacted at about 135° C. and about 15 mm Hg for about 1.5 hours.

To perform the second stage of the reaction, about 266 grams of partially hardened soybean methyl esters (0.9 mole) and about 1.4 grams of potassium carbonate catalyst (0.01 mole) are added to the reactor. This mixture is reacted at about 135° C. and about 2 mm Hg for an additional four hours. The reaction is sampled at this point and the samples are analyzed by supercritical fluid chromatography using an internal standard to calibrate the results. The crude reaction product has an octaester content of about 66% on a methyl ester and soap free basis and an average of about 7.56 of ester groups per polyol ester molecule.

At this point, 0.14 grams of the encapsulated potassium methylate catalyst (0.002 mole) are added. This mixture is reacted at about 135° C. and about 8 mm Hg for about one hour. Another sample is analyzed by supercritical fluid chromatography as before and is found to contain about 83% octaester on a methyl ester and soap free basis with an average of fatty acyl groups per sucrose molecule of about 7.81.

What is claimed is:

1. A stable, highly alkaline, transesterification catalyst composition comprising normally unstable, highly alkaline transesterification catalyst selected from the group consisting of alkali metal hydride, alkali metal alkoxide, and mixtures thereof surrounded by solid fatty acid ester.

2. A stable, highly alkaline transesterification catalyst composition comprising normally unstable, highly transesterification catalyst surrounded by solid fatty acid ester, said catalyst being selected from the group consisting of sodium and potassium alkoxides containing from one to about four carbon atoms.

3. The composition of claim 2 wherein said catalyst is sodium or potassium methoxide.

4. The composition of claim 3 wherein the catalyst is from about 5% to about 40% of said composition.

5. The composition of claim 3 wherein said catalyst is potassium methoxide.

6. The composition of claim 1 wherein the catalyst is from about 1% to about 60% of said composition.

7. The composition of claim 6 wherein the catalyst is from about 5% to about 40% of the composition.

8. The composition of claim 7 wherein the catalyst is from about 10% to about 20% of said composition.

9. The composition of claim 6 wherein said catalyst is an alkali metal alkoxide.

10. A composition comprising a stable, highly alkaline transesterification catalyst surrounded by a solid fatty acid ester, said catalyst being selected from the group consisting of sodium and potassium alkoxides containing from one to about four carbon atoms, and comprising from about 1% to about 60% of the composition.

11. The composition of claim 10 wherein said catalyst is sodium or potassium methoxide.

12. The composition of claim 11 wherein said ester is derived from fatty acid containing from about 12 to about 22 carbon atoms and volatile alcohol.

13. The composition of claim 12 wherein said fatty acid contains from about 16 to about 22 carbon atoms and said alcohol is selected from the group consisting of fatty alcohols containing from one to about four carbon atoms, said fatty alcohols substituted with alkoxy groups containing up to about 5 carbon atoms, benzyl alcohol, and mixtures thereof.

14. The composition of claim 12 wherein said fatty acid ester consists of saturated fatty acid esters, or a mixture of saturated and unsaturated fatty acid esters.

* * * * *